(12) United States Patent
Lin et al.

(10) Patent No.: US 10,588,932 B2
(45) Date of Patent: Mar. 17, 2020

(54) METHOD FOR PROMOTING HAIR GROWTH USING BANANA STAMEN EXTRACT

(71) Applicant: TCI CO., LTD., Taipei (TW)

(72) Inventors: Yung-Hsiang Lin, Taipei (TW); Yu-Ting Lin, Taipei (TW)

(73) Assignee: TCI CO., LTD., Taipei (TW)

(*) Notice: Subject to any disclaimer, the term of this patent is extended or adjusted under 35 U.S.C. 154(b) by 0 days.

(21) Appl. No.: 16/174,948

(22) Filed: Oct. 30, 2018

(65) Prior Publication Data

US 2019/0358284 A1 Nov. 28, 2019

(30) Foreign Application Priority Data

May 25, 2018 (TW) .............................. 107117998 A

(51) Int. Cl.
| | |
|---|---|
| *A61K 36/88* | (2006.01) |
| *A61K 8/9794* | (2017.01) |
| *A23L 33/105* | (2016.01) |
| *A61Q 7/00* | (2006.01) |

(52) U.S. Cl.
CPC ............ *A61K 36/88* (2013.01); *A23L 33/105* (2016.08); *A61K 8/9794* (2017.08); *A61Q 7/00* (2013.01); *A23V 2002/00* (2013.01); *A61K 2236/331* (2013.01)

(58) Field of Classification Search
None
See application file for complete search history.

(56) References Cited

U.S. PATENT DOCUMENTS

| | | | |
|---|---|---|---|
| 2016/0082067 A1* | 3/2016 | Su ......................... | A61K 9/4816 424/451 |
| 2018/0228860 A1* | 8/2018 | Lin ........................ | A61K 36/88 |
| 2019/0153013 A1* | 5/2019 | Lin ........................ | C07H 17/02 |

FOREIGN PATENT DOCUMENTS

| | | | |
|---|---|---|---|
| JP | 2010 155829 A | * | 7/2010 |
| JP | 2015 017067 A | * | 1/2015 |

OTHER PUBLICATIONS

Rao M. et al. Taxonomical, Phytochemical and Pharmacological Reviews of *Musa sapientum* var. *Paradisiaca*. Research J of Pharmacy and Technology 7(11)1356-61, Nov. 2014. (Year: 2014).*

Yusuf M. et al. Herbal Gel Containing Corm Extract of Pisang Kepok Promote Hair Growth of Rabbit. European J of Biomedical and Pharmaceutical Sciences 4(4)27-32, Apr. 2017. (Year: 2017).*

* cited by examiner

*Primary Examiner* — Ralph J Gitomer
(74) *Attorney, Agent, or Firm* — WPAT, PC

(57) ABSTRACT

The present invention relates to a use of a banana stamen extract for promoting hair growth. The banana stamen extract according to the present invention promotes gene expression of VEGF and IGF1 to enhance the proliferation level of hair follicles, so that the density of hairs grown is increased. In addition, the banana stamen extract also inhibits gene expression of SRD5A1, SRDA2 and AR to decrease hair loss, and promote the gene expression of KROX20 so as to significantly enhance hair growth.

11 Claims, 5 Drawing Sheets

Specification includes a Sequence Listing.

METHOD FOR PROMOTING HAIR GROWTH USING BANANA STAMEN EXTRACT

CROSS-REFERENCE TO RELATED APPLICATION

This application claims priority of Taiwan patent application No. 107117998, filed on May 25, 2018, the content of which is incorporated herein in its entirety by reference.

BACKGROUND OF THE INVENTION

1. Field of the Invention

The present invention relates to a method for promoting hair growth, and more particularly to a method for promoting hair growth by administering a banana stamen extract.

2. The Prior Art

There are many reasons for hair thinning or excessive shedding, such as genetic factors, during pregnancy, major surgery, weight loss, body hormones, iron changes, or heavy physical and mental stress. Influencing factors, in addition, excessive combing hair and unhealthy scalp are also the reasons. Hair thinning or severe shedding, resulting in uneven hair distribution, appearance collapse, and the formation of different forms of baldness, may seriously affecting the personal beauty, and also the personal self-confidence, is one of the common problems of modern people.

In order to solve the problem of hair sparse or severe hair loss, against different formation reasons, there are many folk prescription or claimed effective treatments, but they all seem not to achieve the better improvement effect. About 90% of the hair is in the growth stage, and about 10% of it is in the rest stage. If we want to effectively improve the hair growth, besides promoting the health of the hair and prolonging the hair growth period, adjusting the proportion and duration of the rest period to avoid the same period or a large number of hairs entering the rest stage. If we have a product that prolongs the growth period, promotes hair growth, and inhibits hair loss, it will maintain a considerable amount of hair and reduce hair thinning or baldness. If the number of hair follicle cells can be further increased, the amount of hair growth can be increased, and the hair growth can be better and completely improved.

However, the current improvement method for hair thinning mainly focuses on maintaining the health of hair follicle mastoid cells, or stimulating hair follicle cells themselves to promote hair growth, and these methods cannot effectively and comprehensively solve the problems of hair loss reduction, and much medication used in these methods has its side effects.

Banana is one of the fruits that Taiwanese people often eat. The flowers they bloom contain the male flowers at the front end, as well as the neutral flowers and female flowers. Only the female flowers can bear fruit, and the male flowers are generally discarded, but later discovered that the banana flower stamens are rich in anthocyanins and contain cyanidin, which inhibits dihydrotestosterone and is used in the care of the prostate. However, there is no relevant research on whether banana stamens can regulate hair loss, hair growth genes, or promote hair follicle cell proliferation.

SUMMARY OF THE INVENTION

To solve the foregoing problem, one objective of the present invention is to provide a method for promoting hair growth, comprising administering to a subject in need thereof a composition comprising a banana stamen extract.

In one embodiment of the present invention, the banana stamen extract is obtained by water extraction of a banana stamen, and the water extraction is performed at a temperature from 35-55° C. for 30-90 minutes.

In one embodiment of the present invention, the banana stamen extract promotes the proliferation of hair follicle cells and increases the density of hair growth.

In one embodiment of the present invention, the banana stamen extract promotes the gene expression of VEGF and IGF1 to enhance the proliferation of hair follicle cells.

In one embodiment of the present invention, the dose of the banana stamen extract is 0.05-0.15 mg/mL, preferably 0.06 to 0.13 mg/mL, more preferably 0.0625 to 0.125 mg/mL.

In one embodiment of the present invention, the banana stamen extract inhibits the gene expression of SRD5A1, SRD5A2 and AR or reduces the reactive oxygen species (ROS) to reduce the hair loss of the subject in need thereof.

In one embodiment of the present invention, the banana stamen extract promotes the gene expression of KROX20 to promote hair growth, and so as to increase the hair growth.

In one embodiment of the present invention, the composition is further added to food, health food or dietary supplements.

In one embodiment of the present invention, the composition is further added to hair cleansing products or hair care products.

The banana stamen extract of the present invention not only promotes hair production, but also inhibits hair loss. While maintaining and increasing the amount of hair, the amount of hair is increased by the proliferation of hair follicle cells so as to increase the density of hair. Therefore, the problem of thinning or falling off of the hair is comprehensively improved, and the hair is densely grown.

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Definition

Figure 1:
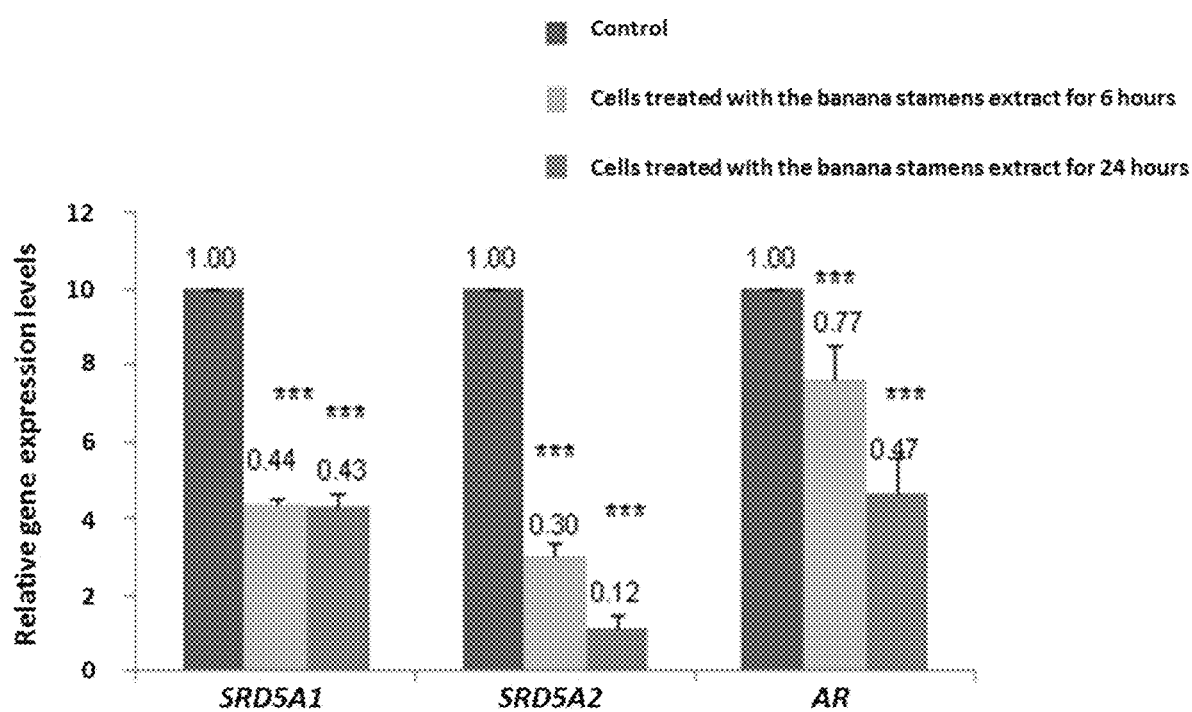
FIG. 1 shows the relative expression levels of hair-loss-related genes (SRD5A1, SRD5A2, and AR) affected by the banana stamen extract in accordance with one embodiment of the present invention.

The data provided in the present invention represent approximated, experimental values that may vary within a range of ±20%, preferably ±10%, and most preferably ±5%.

Example 1

Preparation of the Banana Stamen Extract

First, the stamens of the banana flower are collected by hand or by machine, and the stamens of the banana flower are washed with water and used. Bananas used in the embodiments of the present invention may include, but are not limited to, *Musa sapientum L.*, *Musa* spp. AAB *Silk*, *Musa* spp. ABB *Bluggoe*, *Musa* spp. AAA *Robusta*, and *Musa* spp. AAB *Bluggoe*, etc., and preferably *Musa paradisiacal*. Then, the banana stamens and water are mixed at a ratio of 1-5:4-20, and then are extracted by cold-sonication at 35-55° C. for 30-90 minutes to obtain the crude extract of banana stamens. Preferably, the ratio of banana stamens to water is 1:4. Preferably, the extraction temperature is 35-50° C. or 40-55° C., and the preferred extraction time is about 30 minutes. The banana extract is then centrifuged and filtered through a 300 mesh screen to obtain the banana flower extract of the present invention.

Example 2

Detection of Hair-Loss-Related Gene Expression Level

Human hair follicle dermal papilla cells (HFDPC, PromoCell) are prepared and cultured in follicle dermal papilla cell growth medium (PromoCell). $1.5 \times 10^5$ HFDPC are cultured in each well of a 6-well plate with 2 mL cultured medium. The cells are separated into three groups, wherein group A is the control group, and group B is the 6-hours test group and group C is the 24-hour test group. Groups B and C are respectively treated with 0.125 mg/mL the banana stamen extract at 37° C. for 6 hours and 24 hours, respectively. Then, the expression levels of hair-loss-related genes in these three groups are determined based on quantitative polymerase chain reaction (referred to as qPCR), respectively.

The cells of these three groups are collected and ribonucleic acid (RNA) is isolated from cells by using an RNA extraction kit (Geneaid) according to the manufacturer's instructions. The isolated RNA is reverse transcribed to complementary deoxyribonucleic acid (cDNA) by using reverse transcriptase (SuperScript® III, Invitrogen). Thereafter, the cDNA is subjected to PCR amplification by using the qPCR kit (KAPA CYBR FAST qPCR Kit (2×), KAPA Biosystems) and the specific primer sets of SRD5A1 gene, SRD5A2 gene, and AR gene (Table 1). β-actin gene is as an internal control. The qPCR was performed with StepOnePlus™ Real-Time PCR Systems to obtain a melting curve and a cycle threshold ($C_T$) of each gene and the $2^{-\Delta\Delta C_T}$ method is used to determine the relative expression levels of the target gene. The PCR conditions were 95° C. for 1 seconds, 60° C. for 20 seconds (40 cycles). The statistically significant difference is determined by the single-tailed student t-test of Excel software, and the standard deviation is determined by the STDEV formula (*p value <0.05; p value <0.01; *p value <0.001). The results of expression level changes of the aforementioned genes are shown in FIG. 1.

TABLE 1

| Genes | primers | Numbers | Primer length (ntds) | Product length (ntds) |
|---|---|---|---|---|
| SRD5A1 | SRD5A1-F | SEQ ID NO: 1 | 20 | 77 |
|  | SRD5A1-R | SEQ ID NO: 2 | 20 |  |
| SRD5A2 | SRD5A2-F | SEQ ID NO: 3 | 17 | 119 |
|  | SRD5A2-R | SEQ ID NO: 4 | 23 |  |
| AR | AR-F | SEQ ID NO: 5 | 20 | 104 |
|  | AR-R | SEQ ID NO: 6 | 20 |  |
| β-actin | β-actin-F | SEQ ID NO: 7 | 21 | 250 |
|  | β-actin-R | SEQ ID NO: 8 | 21 |  |

As showing in FIG. 1, after treated with the banana stamen extract of the present invention, the relative gene expression levels of SRD5A1 is greatly reduced by about 57% in the, SRD5A2 is significantly reduced by about 70-88%, and AR is reduced by 23-53%. Among them, the results of the 24-hour test group are better than the 6-hour test group, and the effect of the 24-hour test on reducing gene expression is better. Since SRD5A1 gene, SRD5A2 gene, and the AR gene are involved in hair loss metabolism, if the expression of such hair-loss-related genes is suppressed, hair loss can be reduced and a large amount of hair can be maintained.

Example 3

Detection of Hair-Growth-Related Gene Expression Level

Human hair follicle dermal papilla cells (HFDPC, PromoCell) are prepared and cultured in follicle dermal papilla cell growth medium (PromoCell). $1.5 \times 10^5$ HFDPC are cultured in each well of a 6-well plate with 2 mL cultured medium. The cells are separated into three groups, wherein group A is the control group, and group B is the 6-hours test group and group C is the 24-hour test group. Groups B and C are respectively treated with 0.125 mg/mL the banana stamen extract at 37° C. for 6 hours and 24 hours, respectively. Then, the expression levels of hair-loss-related genes in these three groups are determined based on quantitative polymerase chain reaction (referred to as qPCR), respectively.

The cells of these three groups are collected and ribonucleic acid (RNA) is isolated from cells by using an RNA extraction kit (Geneaid) according to the manufacturer's instructions. The isolated RNA is reverse transcribed to complementary deoxyribonucleic acid (cDNA) by using reverse transcriptase (SuperScript® III, Invitrogen). Thereafter, the cDNA is subjected to PCR amplification by using the qPCR kit (KAPA CYBR FAST qPCR Kit (2×), KAPA Biosystems) and the specific primer sets of KROX20 gene (Table 2). β-actin gene is as an internal control. The qPCR was performed with StepOnePlus™ Real-Time PCR Systems to obtain a melting curve and a cycle threshold ($C_T$) of each gene and the $2^{-\Delta\Delta C_T}$ method is used to determine the relative expression levels of the target gene. The PCR conditions were 95° C. for 1 seconds, 60° C. for 20 seconds (40 cycles). The statistically significant difference is determined by the single-tailed student t-test of Excel software, and the standard deviation is determined by the STDEV formula (*p value <0.05; p value <0.01; *p value <0.001). The results of expression level changes of the aforementioned gene are shown in FIG. 2.

TABLE 2

| Genes | primers | Numbers | Primer length (ntds) | Product length (ntds) |
|---|---|---|---|---|
| KROX20 | KROX20 -F | SEQ ID NO: 9 | 20 | 134 |
|  | KROX20 -R | SEQ ID NO: 10 | 20 |  |

Figure 2:
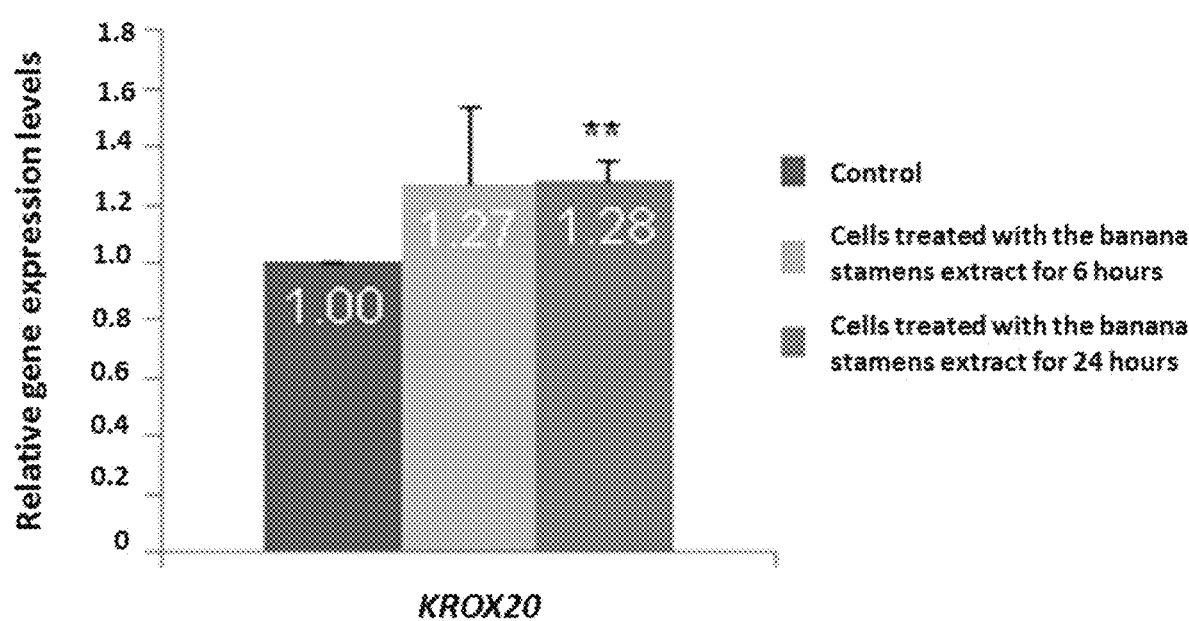
FIG. 2 shows the relative expression levels of hair-growth-related gene (KROX20) affected by the banana stamen extract in accordance with one embodiment of the present invention.

As showing in FIG. 2, after treated with the banana stamen extract of the present invention, the relative gene expression levels of KROX20 is enhanced by 28% (i.e. 1.28 fold). The effect of the 6-hour test and 24-hour test on reducing gene expression is equivalent. Since KROX20 gene is involved in the growth of hair, the growth of hair can be promoted by the banana stamen extract of the present invention.

Example 4

Detection of Hair Follicle Cell Proliferation-Related Gene Expression Level

Human hair follicle dermal papilla cells (HFDPC, PromoCell) are prepared and cultured in follicle dermal papilla cell growth medium (PromoCell). $1.5 \times 10^5$ HFDPC are cultured in each well of a 6-well plate with 2 mL cultured medium. The cells are separated into three groups, wherein group A is the control group, and group B is the 6-hours test group and group C is the 24-hour test group. Groups B and C are respectively treated with 0.125 mg/mL the banana stamen extract at 37° C. for 6 hours and 24 hours, respectively. Then, the expression levels of hair-loss-related genes in these three groups are determined based on quantitative polymerase chain reaction (referred to as qPCR), respectively.

The cells of these three groups are collected and ribonucleic acid (RNA) is isolated from cells by using an RNA extraction kit (Geneaid) according to the manufacturer's instructions. The isolated RNA is reverse transcribed to complementary deoxyribonucleic acid (cDNA) by using reverse transcriptase (SuperScript® III, Invitrogen). Thereafter, the cDNA is subjected to PCR amplification by using the qPCR kit (KAPA CYBR FAST qPCR Kit (2×), KAPA Biosystems) and the specific primer sets of VEGF gene, and IGF1 gene (Table 3). β-actin gene is as an internal control. The qPCR was performed with StepOnePlus™ Real-Time PCR Systems to obtain a melting curve and a cycle threshold ($C_T$) of each gene and the $2^{-\Delta\Delta C_T}$ method is used to determine the relative expression levels of the target gene. The PCR conditions were 95° C. for 1 seconds, 60° C. for 20 seconds (40 cycles). The statistically significant difference is determined by the single-tailed student t-test of Excel software, and the standard deviation is determined by the STDEV formula (*p value <0.05; p value <0.01; *p value <0.001). The results of expression level changes of the aforementioned genes are shown in FIG. 3.

TABLE 3

| Genes | primers | Numbers | Primer length (ntds) | Product length (ntds) |
|---|---|---|---|---|
| VEGF | VEGF -F | SEQ ID NO: 11 | 20 | 280 |
|  | VEGF -R | SEQ ID NO: 12 | 20 |  |
| IGF1 | IGF1-F | SEQ ID NO: 13 | 23 | 210 |
|  | IGF1-R | SEQ ID NO: 14 | 21 |  |

Figure 3:
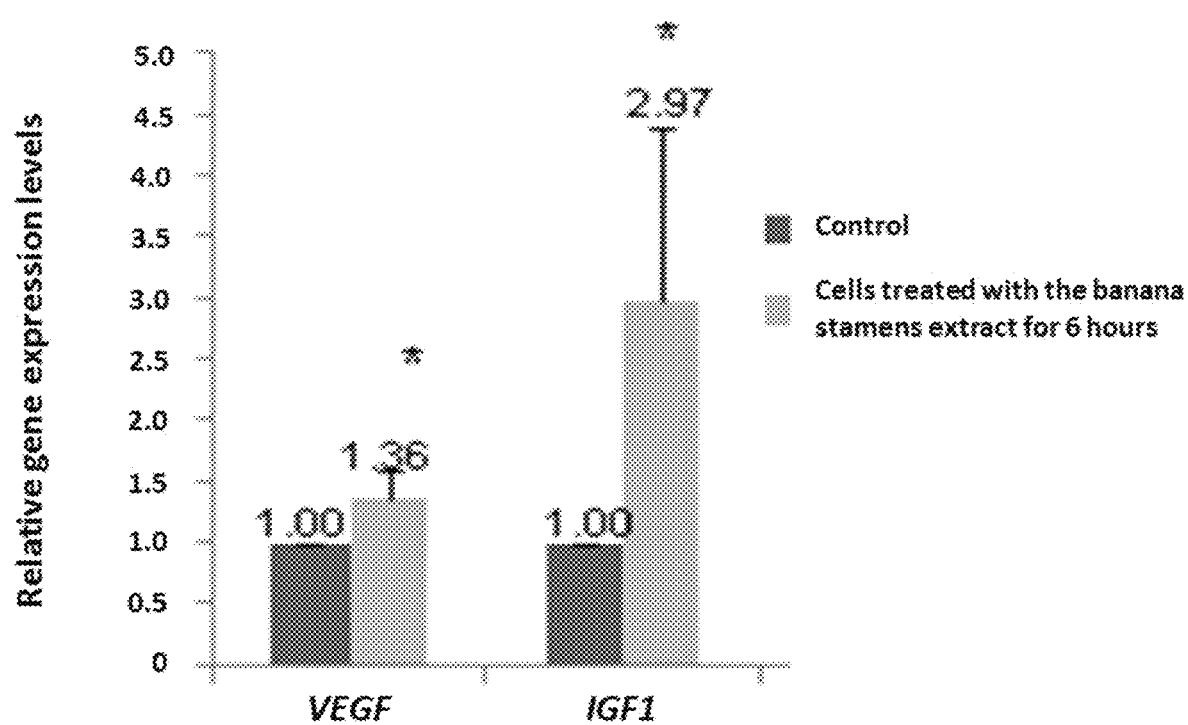
FIG. 3 shows the relative expression levels of HFDPC-angiogenesis-related genes (VEGF and IGF1) affected by the banana stamen extract in accordance with one embodiment of the present invention.

As showing in FIG. 3, after treated with the banana stamen extract of the present invention, the relative gene expression levels of VEGF is enhanced by 36% (i.e. 1.36 fold), and IGF1 is greatly enhanced by 197% (i.e. 2.97 fold). Since VEGF gene is involved in angiogenesis, and IGF1 is involved in the growth of cells, the increase in the expression of VEGF gene and IGF1 gene has a promoting effect on the growth of cells. Therefore, the banana stamen extract of the present invention can further promote the growth of hair follicle cells by enhancing the expression of VEGF gene, and IGF1 gene.

Example 5

Analysis of Hair Follicle Cell Proliferation

Human hair follicle dermal papilla cells (HFDPC, PromoCell) are prepared and cultured in follicle dermal papilla cell growth medium (PromoCell). 5000 HFDPC are cultured in each well of a 96-well plate at 37° C. for 2 hours, and then subjected to analyze the cell proliferation.

The cell proliferation analysis is performed by the BrdU Cell proliferation ELISA kit (Roche, 11647229001). The cultured HFDPC are separated into three groups, wherein group A is the negative control group, and group B is the test group with 0.125 mg/mL the banana stamen extract and group C is the test group with 0.625 mg/mL the banana stamen extract. 100 µL of Fetal bovine serum (FBS) is added into the control groups, and 100 µL of the banana stamen extract (0.0625 mg/mL and 0.125 mg/mL), which is prepared in the foregoing Example 1, is added into the test group. And then, 10 µL of BrdU (100 µM) is added into to each group, and the cells are cultured at 37° C. for 24 hours.

Figure 4:
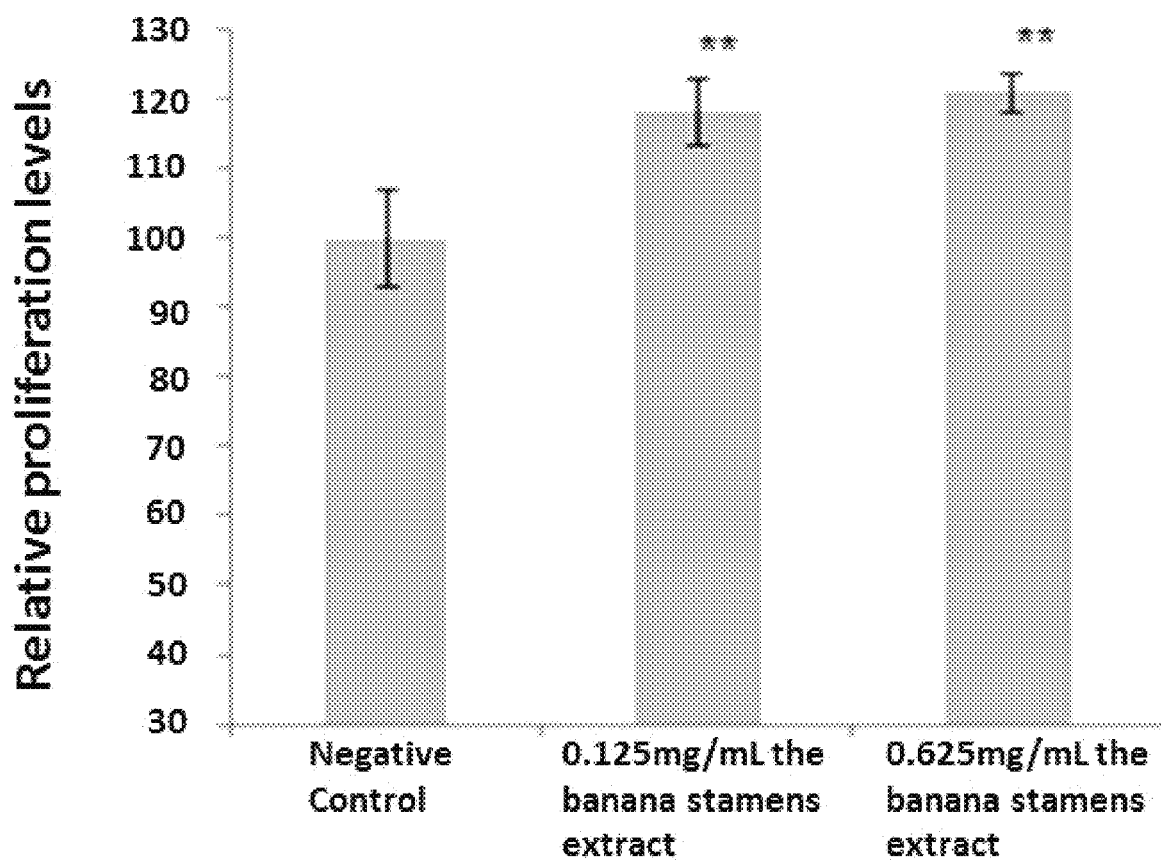
FIG. 4 shows relative proliferation levels of HFDPC treated with or without the banana stamen extract in accordance with one embodiment of the present invention.

The supernatant is removed and 200 µL of FixDeant solution is added into each well of the 96-well plate, and reacted at room temperature for 30 minutes. The FixDeant solution is then removed and the cells is washed once with 1× phosphate buffered saline (PBS) and then 100 µL of the anti-BrdU-POD antibody reaction solution is added into each well of the 96-well plate, and reacted at room temperature for 90 minutes. After the reaction, the unreacted antibody reaction solution was removed, and each well of the cells is washed with 200 to 300 µL of the washing solution. The washing solution is then removed, and 100 µL of the substrate solution is added into each well of the 96-well plate, and reacted at room temperature for 5 to 30 minutes. Finally, 25 µL of 1 M sulfuric acid is added to each well of the 96-well plate, and the reaction is shaken at 300 rpm for about 1 minute. The absorbance of each well solution at a wavelength of 450 nm is measured after the reaction. The statistically significant difference is determined by the student t-test of Excel software. The results of expression level changes of the aforementioned genes are shown in FIG. 4. (*p value <0.05; p value <0.01; *p value <0.001)

As showing in FIG. 4, after treated with the banana stamen extract of the present invention, no matter the dose is 0.0625 mg/mL or 0.125 mg/mL, the amount of HFDPC is significantly increased. Compared with the negative control group, the amount can be greatly increased to about 20%. Therefore, the banana stamen extract of the present invention can indeed increase the growth of hair follicle cells, which in turn increases the density of hair growth.

Example 6

Detection of the ROS Production Induced by Hydrogen Peroxide

Human hair follicle dermal papilla cells (HFDPC, PromoCell) are prepared and cultured in follicle dermal papilla cell growth medium (PromoCell). $1\times10^5$ HFDPC are cultured in each well of a 6-well plate with 2 mL cultured medium at 37° C. for 24 hours, and then the culture medium are removed.

The cells are separated into three groups and incubated at 37° C. for 1 hour, wherein group A is the negative control group, and group B is the control group with 1 mM hydrogen peroxide ($H_2O_2$), and group C is the test group with 1 mM $H_2O_2$ and 0.0625 mg/mL and 0.125 mg/mL the banana stamen extract prepared by the foregoing Example 1. Each group is repeated twice.

Thereafter, 5 μg/mL DCFH-DA (Sigma, SI-D6883-50MG) is added into each well, and the cells are cultured at 37° C. for 15 minutes. The cells are treated with $H_2O_2$ at 37° C. for 1 hour, and then are washed twice with 1 mL 1×PBS. 200 μL of trypsin is added and allowed to react in the dark for 5 minutes. The culture medium containing the cells is then transferred to a 1.5 mL eppendorf and centrifuged at 400×g for 10 minutes. After centrifugation, the supernatant is removed and the pellet is washed once with 1×PBS. After centrifugation at 400×g for another 10 minutes, the supernatant is removed, and the pellet is re-dissolved in 1 mL of 1×PBS. Next, the fluorescence signal value of DCFH-DA is detected by flow cytometry (Beckman) under the excitation wavelength of 450-490 nm and the emission wavelength of 510-550 nm. Finally, the statistically significant difference is determined by the student t-test of Excel software (*p value <0.05; p value <0.01; *p value <0.001). The results are shown in FIG. 5.

Figure 5:
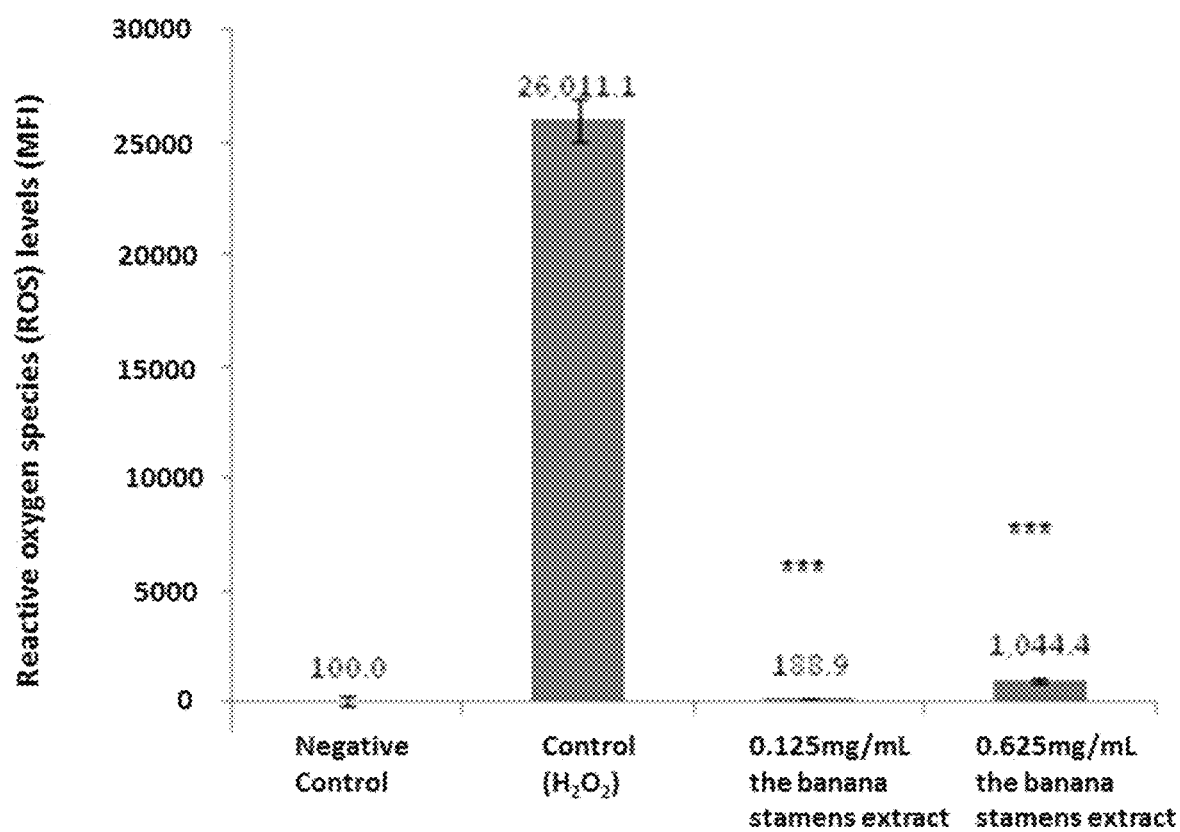
FIG. 5 shows the relative levels of ROS in HFDPC treated with or without the banana stamen extract in accordance with one embodiment of the present invention.

As showing in FIG. 5, after treated with the banana stamen extract of the present invention, the active oxidizing substance (ROS) induced by $H_2O_2$ is greatly reduced to almost disappear and is equivalent to the negative control group. It is apparent that the banana stamen extract of the present invention has excellent antioxidant ability and can improve the occurrence of hair loss.

According to the above tests, the banana stamen extract of the present invention not only promotes hair production, but also inhibits hair loss. While maintaining and increasing the amount of hair, the amount of hair is increased by the proliferation of hair follicle cells so as to increase the density of hair. Therefore, the problem of thinning or falling off of the hair is comprehensively improved, and the hair is densely grown.

In addition, the bananas stamen extract of the present invention is further added to a food, a health food or a dietary supplement, or further is used in a hair cleansing product or a hair care product. When the banana stamen extract of the present invention is prepared as a composition, the composition is further added into a carrier or other adjuvant known in the art. The dosage form of the composition can be, but is not limited to, a solution, a capsule, or a tablet.

---

What is claimed is:

1. A method for promoting hair growth, comprising administering to a subject in need thereof a composition comprising a banana stamen extract.

2. The method according to claim 1, wherein the banana stamen extract is obtained by water extraction of a banana stamen.

3. The method according to claim 2, wherein the water extraction is performed at a temperature from 35 to 55° C.

4. The method according to claim 1, wherein the banana stamen extract promotes the proliferation of hair follicle cells and increases the density of hair growth.

5. The method according to claim 1, wherein the banana stamen extract in the composition is at a concentration of 0.05-0.15 mg/mL.

6. The method according to claim 1, wherein the banana stamen extract promotes the gene expression of VEGF and IGF1.

7. The method according to claim 4, wherein the banana stamen extract promotes the gene expression of VEGF and IGF1.

8. The method according to claim 1, wherein the banana stamen extract inhibits the gene expression of SRD5A1, SRD5A2 and AR or reduces the reactive oxygen species (ROS) to reduce the hair loss of the subject in need thereof.

9. The method according to claim 1, wherein the banana stamen extract promotes the gene expression of KROX20 to promote hair growth.

10. The method according to claim 1, wherein the composition is further added to food, health food or dietary supplements.

11. The method according to claim 1, wherein the composition is further added to hair cleansing products or hair care products.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial sequence
<220> FEATURE:
<223> OTHER INFORMATION: PCR primer

<400> SEQUENCE: 1
tacgggcatc ggtgcttaat                                              20

<210> SEQ ID NO 2
<211> LENGTH: 20
<212> TYPE: DNA
<213> ORGANISM: Artificial sequence
<220> FEATURE:
<223> OTHER INFORMATION: PCR primer

<400> SEQUENCE: 2
gccattgtac acgccaacag                                              20

<210> SEQ ID NO 3
<211> LENGTH: 17
<212> TYPE: DNA
<213> ORGANISM: Artificial sequence
<220> FEATURE:
<223> OTHER INFORMATION: PCR primer

<400> SEQUENCE: 3
tgccttcctt cgcggtg                                                 17

<210> SEQ ID NO 4
<211> LENGTH: 23
```

```
<212> TYPE: DNA
<213> ORGANISM: Artificial sequence
<220> FEATURE:
<223> OTHER INFORMATION: PCR primer

<400> SEQUENCE: 4
cacaaatgtc ctgtggaagt aat                                           23

<210> SEQ ID NO 5
<211> LENGTH: 20
<212> TYPE: DNA
<213> ORGANISM: Artificial sequence
<220> FEATURE:
<223> OTHER INFORMATION: PCR primer

<400> SEQUENCE: 5
ggtgagcaga gtgccctatc                                               20

<210> SEQ ID NO 6
<211> LENGTH: 20
<212> TYPE: DNA
<213> ORGANISM: Artificial sequence
<220> FEATURE:
<223> OTHER INFORMATION: PCR primer

<400> SEQUENCE: 6
gcagtctcca aacgcatgtc                                               20

<210> SEQ ID NO 7
<211> LENGTH: 21
<212> TYPE: DNA
<213> ORGANISM: Artificial sequence
<220> FEATURE:
<223> OTHER INFORMATION: PCR primer

<400> SEQUENCE: 7
catgtacgtt gctatccagg c                                             21

<210> SEQ ID NO 8
<211> LENGTH: 21
<212> TYPE: DNA
<213> ORGANISM: Artificial sequence
<220> FEATURE:
<223> OTHER INFORMATION: PCR primer

<400> SEQUENCE: 8
ctccttaatg tcacgcacga t                                             21

<210> SEQ ID NO 9
<211> LENGTH: 20
<212> TYPE: DNA
<213> ORGANISM: Artificial sequence
<220> FEATURE:
<223> OTHER INFORMATION: PCR primer

<400> SEQUENCE: 9
tttgtgcacc agctgtctga                                               20

<210> SEQ ID NO 10
<211> LENGTH: 20
<212> TYPE: DNA
<213> ORGANISM: Artificial sequence
<220> FEATURE:
<223> OTHER INFORMATION: PCR primer

<400> SEQUENCE: 10
```
ttgatcatgc catctccggc                    20

<210> SEQ ID NO 11
<211> LENGTH: 20
<212> TYPE: DNA
<213> ORGANISM: Artificial sequence
<220> FEATURE:
<223> OTHER INFORMATION: PCR primer

<400> SEQUENCE: 11
ccttgctgct ctacctccac                    20

<210> SEQ ID NO 12
<211> LENGTH: 20
<212> TYPE: DNA
<213> ORGANISM: Artificial sequence
<220> FEATURE:
<223> OTHER INFORMATION: PCR primer

<400> SEQUENCE: 12
atctgcatgg tgatgttgga                    20

<210> SEQ ID NO 13
<211> LENGTH: 23
<212> TYPE: DNA
<213> ORGANISM: Artificial sequence
<220> FEATURE:
<223> OTHER INFORMATION: PCR primer

<400> SEQUENCE: 13
tcctcctcgc atctcttcta cct                23

<210> SEQ ID NO 14
<211> LENGTH: 21
<212> TYPE: DNA
<213> ORGANISM: Artificial sequence
<220> FEATURE:
<223> OTHER INFORMATION: PCR primer

<400> SEQUENCE: 14
gaagcagcac tcatccacga t                  21